United States Patent [19]
Cain

[11] Patent Number: 5,984,368
[45] Date of Patent: *Nov. 16, 1999

[54] PATIENT CONDITION AND PAIN LOCATION AND INTENSITY COMMUNICATION APPARATUS AND METHOD

[75] Inventor: John R. Cain, Topeka, Kans.

[73] Assignee: Quality Medical Communications, Inc., Topeka, Kans.

[*] Notice: This patent is subject to a terminal disclaimer.

[21] Appl. No.: 09/028,012

[22] Filed: Feb. 23, 1998

Related U.S. Application Data

[63] Continuation-in-part of application No. 08/744,434, Nov. 8, 1996, Pat. No. 5,720,502.

[51] Int. Cl.[6] .................................................. B42D 15/00
[52] U.S. Cl. .............................. 283/115; 283/70; 283/900
[58] Field of Search ................................ 283/115, 601, 283/70, 900, 67; 434/262, 274, 267, 112, 270, 272

[56] References Cited

U.S. PATENT DOCUMENTS

| | | | |
|---|---|---|---|
| 3,858,351 | 1/1975 | Porter | 46/116 |
| 4,165,890 | 8/1979 | Leff | 283/46 X |
| 4,464,122 | 8/1984 | Fuller et al. | 434/262 |
| 4,561,851 | 12/1985 | Ferreira et al. | 434/272 |
| 4,624,642 | 11/1986 | Ferrara | 434/274 |
| 4,762,494 | 8/1988 | Woods | 434/236 |
| 4,795,348 | 1/1989 | Garthwaite | 434/112 |
| 4,865,549 | 9/1989 | Sonsteby | 434/262 |
| 4,869,531 | 9/1989 | Rees | 283/67 |
| 5,083,816 | 1/1992 | Folga et al. | 283/81 |
| 5,102,169 | 4/1992 | Mayfield | 283/115 |
| 5,498,034 | 3/1996 | Ford | 283/70 X |
| 5,720,502 | 2/1998 | Cain | 283/900 X |
| 5,758,096 | 5/1998 | Barsky et al. | 283/900 X |

Primary Examiner—Willmon Fridie, Jr.
Attorney, Agent, or Firm—Litman, Kraai & Brown L.L.C.

[57] ABSTRACT

The present invention comprises a preprinted chart, or, in the case of software, a programmed screen display, on which is displayed front and back silhouettes of a patient. Alongside the silhouettes are provided a number of series of icons which illustrate various patient conditions, such as burn, cut, bruise, etc. with at least some of the icon series being color coded to indicate pain intensity. The icons can be moved to the silhouettes. In an alternative version, the chart can be folded in half with the bottom half inserted into a transparent plastic sleeve and the top half folded over the bottom half to provide confidentiality. Other chart embodiments include a small, portable patient dietary guideline chart, a tactile pain communicator with touch coded pain intensity indicators and a group therapy emotional pain communicator.

28 Claims, 10 Drawing Sheets

Fig. 1.

Patient _____
Physician _____

INSTRUCTIONS:
1. Locate pain site on body diagram.
2. Pull appropriate sticker for pain type.
3. Place sticker on pain site.
4. Green Sticker - no pain.

PAIN INTENSITY
RED – Excruciating
ORANGE – intense
YELLOW – Discomforting
BLUE – Mild

PAIN SITE

BONE

BURN

CUT

NUMBNESS (No Feeling)

WEIGHT BEARING (As Tolerable)

DO NOT TOUCH

PAIN

NO PAIN

PATIENT AT SLEEP

NOTHING BY MOUTH

24-HOUR PAIN INTENSITY CHART

| Hours of Day | 4 | 8 | 12 | 4 | 8 | 12 |
|---|---|---|---|---|---|---|
| 10 | . | . | . | . | . | . |
| 5 | . | . | . | . | . | . |
| 0 | . | . | . | . | . | . |

Notes:

Fig. 4.

QUALITY CARE COMMUNICATOR™

Hearing Impaired | Choking | Oxygen | Bed Restraint | 1 Person Transfer | Wheelchair | Heel Protection | Range of Motion | Pillow | Wedge | Non Weight Bearing | Skin Risk | Decub | Loss of Feeling | Bone | | PAIN INTENSITY | | | Do Not Resuscitate
--- | --- | --- | --- | --- | --- | --- | --- | --- | --- | --- | --- | --- | --- | --- | --- | --- | --- | --- | ---
| | O₂ | | | | | ROM | Pillow | Wedge | NON WB | Skin Risk | Decub | Loss Feeling | Bone | Excruciating 3 | Moderate 2 | Mild 1 | | DNR Speech Impaired | Dentures | Force & Mouth | Personal Alarm | 2 Person Transfer | Walker | Elbow Protector | Range of Motion | | | Non Weight Bearing | Skin Risk | Decub | Loss of Feeling | Bone | | | | | Advance Directive
| | NPO | | | | | ROM | Pillow | Wedge | NON WB | Skin Risk | Decub | Loss Feeling | Bone | Excruciating 3 | Moderate 2 | Mild 1 | | ADV DIR Vision Impaired | Diabetic | Bed Falls | Lift Assist | Cane | Restorative Device | Range of Motion | | | | | Falls | Skin Risk | Bruise | Skin Tear | | | | |
| Diabetic | | | | RA Device | ROM | Pillow | Wedge | Falls | Skin Risk | Bruise | Skin Tear | Excruciating 3 | Moderate 2 | Mild 1

Glasses | Bowel & Bladder | Hachotomy | Elopement | Communications Board | Hand Roll | Restorative Device | Range of Motion | | | | RISK Falls | Skin Risk | Bruise | Skin Tear | Status Ulcer | | | |
I&O | | | | PIX Board | | RA Device | ROM | Pillow | Elevated Bed | RISK Falls | Skin Risk | Bruise | Skin Tear | Cut | Fluid Alert | Allergies B&B | TRACH | | | | | | | | | RISK Bruise | Turning Q2H | Bruise | Stasis Ulcer | | FLUID ALERT | ALLERGIES

---

Personal Care  102    P.O.C. Date _____

| | Independent | Supervised | Assisted | Dependent |
| --- | --- | --- | --- | --- |
| Dressing | I | S | A | D |
| Bathing | I | S | A | D |
| Grooming | I | S | A | D |
| Eating | I | S | A | D |
| Ambulation | I | S | A | D |
| Toileting | I | S | A | D |

☐ Catheter ☐ Continent ☐ Incontinent
Personal Laundry: ☐ Facility ☐ Family
Cognitive Status: ☐ Oriented ☐ Confused
Mood and Behavior: ☐ Anxious ☐ Sad/Depressed
Language: ☐ English ☐ Spanish ☐ _____
Special Equipment:
_____ Foot Board   _____ Special Mattress
_____ Bed Cradle   _____ Trapeze   _____ Other _____
Restorative Nursing: _____

Special Care Instructions

Combative   ☐ Verbal   ☐ Physical
☐ OT       ☐ Speech       ☐ Beauty Shop
☐ PT       ☐ Podiatrist   ☐ Activities
☐ Dining

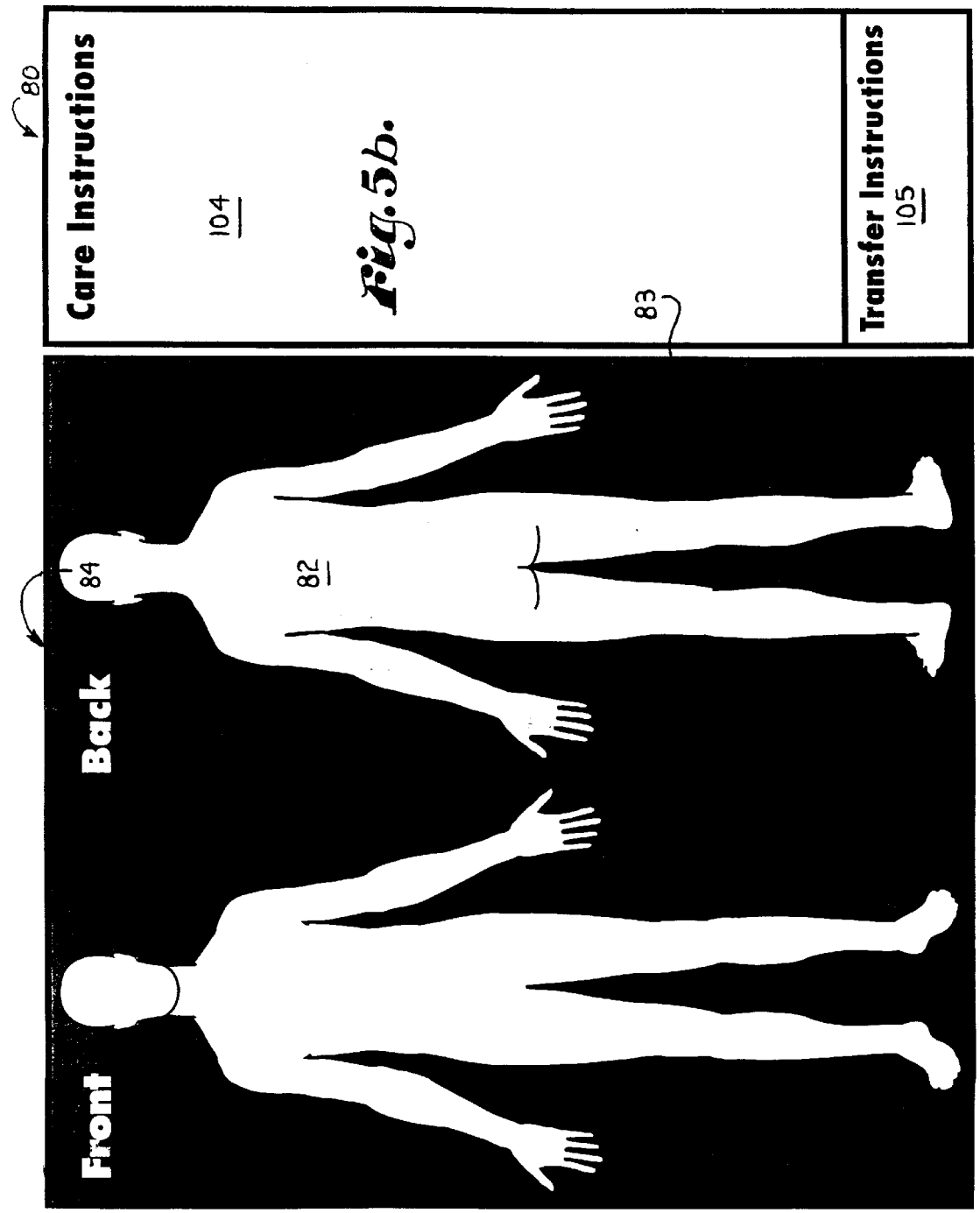

Fig. 5c.

NAME ←105

106↙

THIS IS A CONFIDENTIAL QUARTERLY CARE PLAN COMMUNICATOR.
FOR STAFF USE ONLY.

PATIENT CONDITION AND PAIN LOCATION AND INTENSITY COMMUNICATION APPARATUS AND METHOD

CROSS REFERENCE TO RELATED APPLICATIONS

This application is a continuation-in-part of application for U.S. Pat. Ser. No. 08/744,434, filed Nov. 8, 1996, now U.S. Pat. No. 5,720,502, entitled PAIN LOCATION AND INTENSITY COMMUNICATION APPARATUS AND METHOD.

BACKGROUND OF THE INVENTION

1. Field of the Invention

The present invention relates generally to a patient condition and pain location and intensity communication apparatus and method, and, more particularly, to a patient communication system, which can be implemented as a two dimensional chart or in a software format, in which a display area including a patient silhouette is provided. A number of removable sticker icons, in the case of the hard copy embodiment, or, in the case of software, of movable digital image icons, of varying colors and indicia, are provided for attaching or moving to the silhouette to provide instantaneous patient condition, pain location and pain intensity information. In the case of a hard copy chart with movable icons, an alternative chart embodiment is designed for folding in half and a transparent plastic sleeve is provided for confidentiality and temporary patient condition information. A second alternative embodiment includes small, portable patient communication charts with movable dietary guideline icons. A third alternative embodiment is a tactile pain communicator which is touch coded to allow a patient to manually indicate pain intensity. A fourth alternative embodiment is a family overlay group pain communicator for group therapy sessions with a psycho-social adviser.

2. Description of the Related Art

Recent trends in hospital and rehabilitation clinic patient care has seen an increasing emphasis on pain management, pain communication and improved patient-professional communication on the part of government, insurance, and health care providers. Guidelines developed by the Agency for Health Care Policies and Procedures mandate better communication between patients and practitioners regarding pain. The result has been formation of QIC (Quality Inpatient Care) Pain Committees at most major hospitals. One goal of such committees has been to improve patient to care giver communication and to minimize unnecessary patient pain.

Such patient to care giver communication is problematical at best. With constant hospital shift changes, in a 24 hour period, an admitted patient will be seen by a minimum of 3 different nurses as well as nurses aids and other hospital personnel. Furthermore, a variety of physicians will typically be involved with caring for a single patient. With each new person coming into contact with the patient, information on the patient's condition must be conveyed in some fashion and charted. Frequently, this means that a sleeping patient must be awakened to answer repetitive and annoying questions. Furthermore, when a patient needs to be moved by hospital staff, the person doing the moving often does not have any idea of the patient's condition. Thus, injuries can be aggravated and/or unnecessary pain caused by hospital personnel who, often inadvertently, place weight or stress on injured limbs or other body parts. Recent trends in the health care industry have increased patient communication problems as more and more nurses aids and other relatively unskilled personnel are performing patient care functions previously reserved for trained nurses and doctors.

A number of prior art attempts have been made to facilitate patient to care giver communication. For example, U.S. Pat. No. 4,165,890 to Ruth Leff, and entitled Communication Aid, is drawn to a series of cards attached to a ring for use by a patient with limited communication ability. Each card communicates a physical need or condition, such as wheelchair, stomach ache, etc. to a second party such as a nurse, nurse's aid, etc.

In U.S. Pat. No. 4,865,549 to Kristi Sonsteby, and entitled Medical Documentation and Assessment Apparatus, a number of modular packets are color coded to represent different anatomical features of a patient, such as cardiovascular, neurological, etc. Matching diagnostic sheets are provided within each packet to place in a patient's file or chart.

In U.S. Pat. No. 4,869,531 to Michael Rees, and entitled Apparatus and Method for Documenting Physical Examinations, a group of pre-printed anatomical stickers are provided upon which an examining physician can directly mark the location, size, shape, etc. of any abnormality.

In U.S. Pat. No. 5,102,169 to Mary Mayfield, and entitled Medication Management System, a number of medications are listed on a time chart and color and shape coded stickers are associated with each medicine on the chart and are attached to the medicine containers as well.

In U.S. Pat. No. 5,498,034 to Betheline Ford, and entitled Patient Care Information System, a photograph of a patient's face is positioned on a chart and any number of patient care icons are positioned proximate the photograph to designate sensory losses, mobility limitations, safety concerns, etc. The photograph is apparently used only for positive identification.

Interestingly, none of these prior art patents is concerned with the communication of the pain causing condition, pain location and pain intensity to an attending care provider. None has provided a simple portable dietary guideline chart with movable icons. None has addressed the problem of providing non-verbal communication of pain conditions between a patient and a care provider. Finally, none has provided a secure, easily used group therapy emotional pain communicator for group patient to counselor communication.

Accordingly, it is clear then, that a need exists for a reliable, practical and inexpensive apparatus and method which permits a patient or a patient attendant to quickly, effectively and accurately communicate patient conditions, patient pain location and/or pain intensity to an attending care provider. The present invention addresses this problem.

SUMMARY OF THE INVENTION

The present invention comprises a preprinted two dimensional chart, or, in the case of software, a programmed screen display, on which is displayed front and back silhouettes of a patient. Above the silhouettes are provided a number of series of icons which illustrate various patient conditions, such as burn, cut, bruise, etc. These or other icons can be color coded, e.g. from yellow to orange to red to indicate pain intensity with yellow being mild and red being excruciating pain. In addition, a number of other icons are provided to indicate areas of no pain, unusual risk conditions, restorative requirements, hearing, speech, vision, dietary restrictions, etc. A personal care area is also provided for quickly and efficiently communicating personal care conditions and concerns. Special Care and Ordinary Care Instruction areas are provided for noting these concerns. A row and column 24 hour patient condition time chart can also be provided on which color coded icons can be placed as well.

In an alternative version of hard copy chart with movable icons, the chart can be folded in half with the bottom half inserted into a transparent plastic sleeve and the top half folded over the bottom half. The sleeve thus provides for confidentiality and also, once the top half of the chart is folded backwards, provides a place for temporary condition icons to be placed over the silhouettes. A second alternative embodiment includes small, portable patient communication charts with movable dietary guideline icons. A third alternative embodiment is a tactile pain communicator in which a number of indicators are touch coded with varying pain intensity indications to allow a patient who is temporarily or permanently incapable of verbal communication to manually indicate pain intensity to a health care provider. A fourth alternative embodiment is a family overlay group pain communicator for group therapy sessions with a psychosocial adviser. In this third embodiment, each patient in a group therapy session is given a chart with respective transparent positions representing each person in the group undergoing therapy. As prompted by the counselor, each member of the group places a negative, color coded, emotional pain intensity icon on the transparent position of the person or persons in the group who cause them emotional pain or a positive, color coded, emotional icon on those persons who give them support or make them feel good/wanted, etc. Each chart is then confidentially turned into the counselor who, by overlaying the charts, can readily pinpoint the person or persons in the group who cause pain or who provided positive support.

OBJECTS AND ADVANTAGES OF THE INVENTION

The principle objects and advantages of the present invention include: providing a patient condition and patient pain communication apparatus and method; providing such an apparatus and method which reliably, quickly and effectively communicates patient conditions, patient health concerns, patient pain sources, pain location and pain intensity from a patient to a health care provider; providing such an apparatus and method in which a patient silhouette is provided on a chart, either in hard copy or on a computer screen display; providing such an apparatus and method in which a number of informational icons are provided for localized attachment to the silhouette with each icon being coded to represent a health condition and/or color coded for pain intensity; providing such an apparatus and method which includes a patient condition time chart for periodic updating by health care personnel; providing, in the case of an alternative hard copy chart with movable icons, a transparent plastic sleeve for receiving a half folded chart to provide for confidentiality and temporary patient condition information; providing such an apparatus and method in a second alternative embodiment which includes small, portable patient communication charts with movable dietary guideline icons; providing such an apparatus and method in a third alternative embodiment which includes a tactile pain communicator with different areas touch coded to allow a patient to manually indicate pain intensity; providing a fourth alternative embodiment in which a family overlay group pain communicator provides emotional pain communication for group therapy sessions with a psychosocial counselor; and providing such an apparatus and method which is economical to manufacture, efficient in operation, and which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an illustration of a patient pain location and intensity chart and associated color coded icon stickers.

FIG. 4 is an illustration of a veterinary version of the pain intensity and location communication apparatus.

FIGS. 5a, 5b and 5c collectively provide an illustration of an alternative patient condition and patient pain location and intensity chart and associated icon stickers which chart is designed for folding in half with a bottom half received in a plastic sleeve.

DETAILED DESCRIPTION OF THE PREFERRED EMBODIMENTS

I. Introduction and Environment

Figure 2:
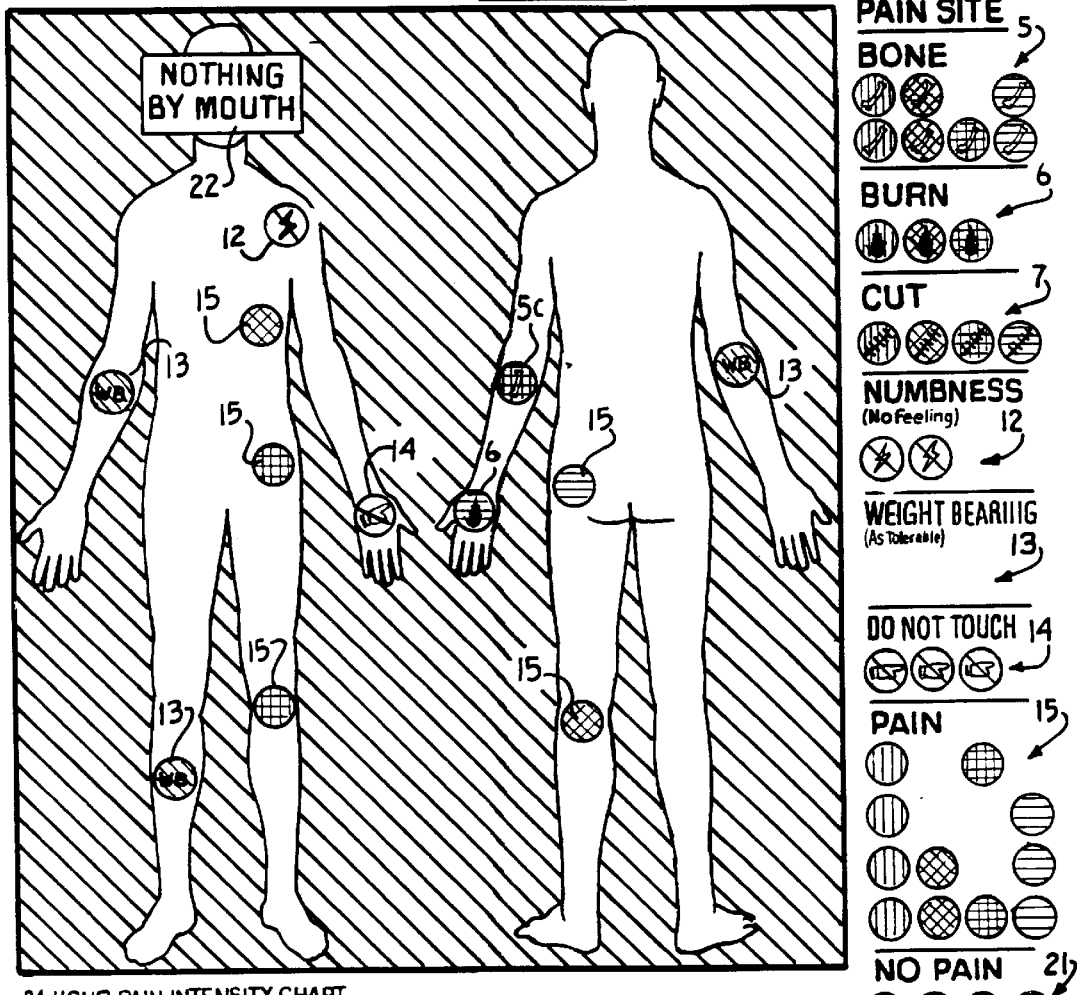
FIG. 2 is an illustration of the chart of FIG. 1 in use by a particular patient to communicate pain location and intensity to an attending health care provider.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "up", "down", "right" and "left" will refer to directions in the drawings to which reference is made. Said terminology will include the words specifically mentioned, derivatives thereof and words of a similar import.

Referring to the drawings in more detail, reference numeral 1 in FIG. 1 generally designates a patient pain intensity and location communication apparatus in the form of a hard copy two dimensional chart including front and back patient silhouettes 2 and 3, respectively, displayed on a colored background in a first display area 4. A plurality of pain source icon groups 5, 6, and 7 are positioned alongside the background 4 in a second display area 8. The icon group 5 indicates a broken bone, the icon group 6 indicates a burn, and the icon group 7 indicates a cut. Each of the icon groups 5–7 is formed by a series of stickers which can be removed from the icon location and placed on the silhouettes in particular locations to indicate pain location. Meanwhile, the icon groups 5–7 are color coded to represent pain intensity, as described in a pain intensity color code guide 11. For example, the broken bone icon group 5 includes a number of stickers 5a, 5b, 5c and 5d with the sticker 5a being blue in color, the sticker 5b being yellow in color, the sticker 5c being orange in color and the sticker 5d being red in color. Thus, from left to right, the stickers 5a to 5d represent increasing pain intensity, as described in the color code guide 11. The icon groups 6 and 7 are similarly color coded. A patient or a person attending the patient can thus select a particular color of icon indicating a particular condition and intensity of pain, remove the icon sticker and place it on the appropriate silhouette 2 or 3, as shown in FIG. 2.

Referring again to FIG. 1, a number of additional icon groups are provided, each including a plurality of stickers. For example, an icon group 12 includes stickers indicating numbness or lack of feeling; an icon group 13 includes stickers indicating weight bearing areas or areas of the patient's body which are capable of supporting weight or of being handled by personnel without intolerable pain; an icon group 14 indicates areas of intense pain or areas which should not be touched; an icon group 15 indicates areas of pain without a specific cause, with the icons within the group 15 being color coded dots, again as indicated in the guide 11; an icon group 21 includes dots indicating areas of no pain, which dots can be of a uniform color different than the colors in the guide 11, e.g. green; and a sticker 22 indicating nothing by mouth to prevent any foods, liquids or medicine to be administered orally can be prominently placed over the mouth of the silhouette 2.

A third display area 23 includes a row and column overall pain intensity indicator chart 24. In the chart 24, column divisions 25 indicate a time line, such as four hour windows in a 24 hour day. Row divisions 26 represent overall pain intensity on a scale from 0 being non-existent or minimal to 10 being maximum. In the second display area 8, an icon group 31 includes stickers of a different color, e.g. black, which can be adhered to the chart 24 in the appropriate time column at the appropriate pain level to keep a running chart of overall pain. An icon group 32 includes stickers labeled as "S" to indicate that the patient was asleep during the monitoring period. This might indicate to personnel to wake the patient during the next monitoring period.

An indicia display area 33 provides an area for patient and physician identification, an area 34 is provided with instructions on use of the chart 1 and an area 35 is provided for miscellaneous notes.

Referring to FIG. 2, an example is provided of the chart 1 in use for a patient with extensive injuries on the right side of his body. For example, an orange sticker 5c indicating an intensely painful broken bone is attached to his left arm; a red burn icon sticker 6 and a "Do Not Touch" icon sticker 14 are attached to his left hand; a numbness icon sticker 12 is attached to his left shoulder; a number of pain stickers 15, which can be of varying pain intensity color codes, are distributed over several portions of the left side of his body; and the "nothing by mouth" sticker 22 is attached over his mouth. By contrast, on both sides of his right arm, as well as his right leg, weight bearing stickers 13 are attached to indicate that these are areas which can support weight with tolerable or no pain.

Still referring to FIG. 2, the row and column pain intensity chart 24 includes a number of stickers 31 placed in five of the six time columns 26. The stickers 31 are positioned to indicate pain intensities from 3 to 6 on a scale of 10. In addition, a sticker 32 is positioned in one of the time columns to indicate that the patient was sleeping during that monitoring period.

Figure 3:
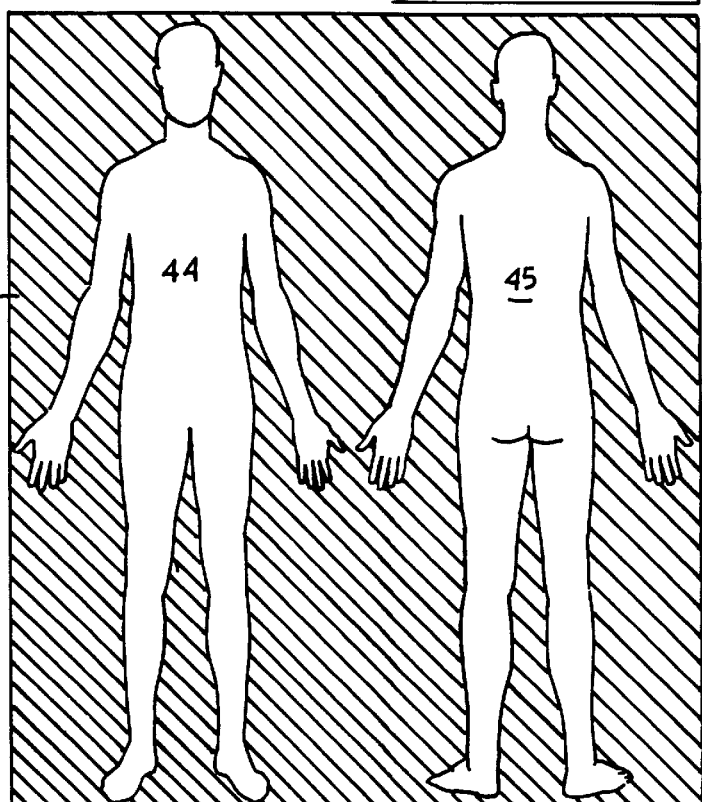
FIG. 3 is an illustration of a software screen display version of the patient pain intensity and location communication apparatus.

Referring to FIG. 3, a computer controlled screen display 41 is programmed to electronically display a chart 42 which is essentially identical in detail to the hard copy chart 1 of FIGS. 1 and 2. The electronic chart 42 includes a first display area 43 with a pair of body silhouettes 44 and 45. A second display are a 51 includes a number of color coded icons 52 which are identical in meaning to the icon groups 5–7, 21, 22, 31 and 32 of FIGS. 1 and 2, and which will not be further described. These icons are selectable via a standard "point and click" method such that they can be dragged from the second display area 51 onto the silhouettes 44 and 45 in the first display area 43 via a cursor 53 and mouse (not shown), or onto a row and column overall pain intensity chart 54 in a third display area 55, as described above with reference to FIGS. 1 and 2. A typical pull down menu 60 is provided above the screen display areas 43 and 51 which pull down menu 60 allows each chart 42 to be stored as a separate graphics file and/or printed in a known manner.

Figure 4:
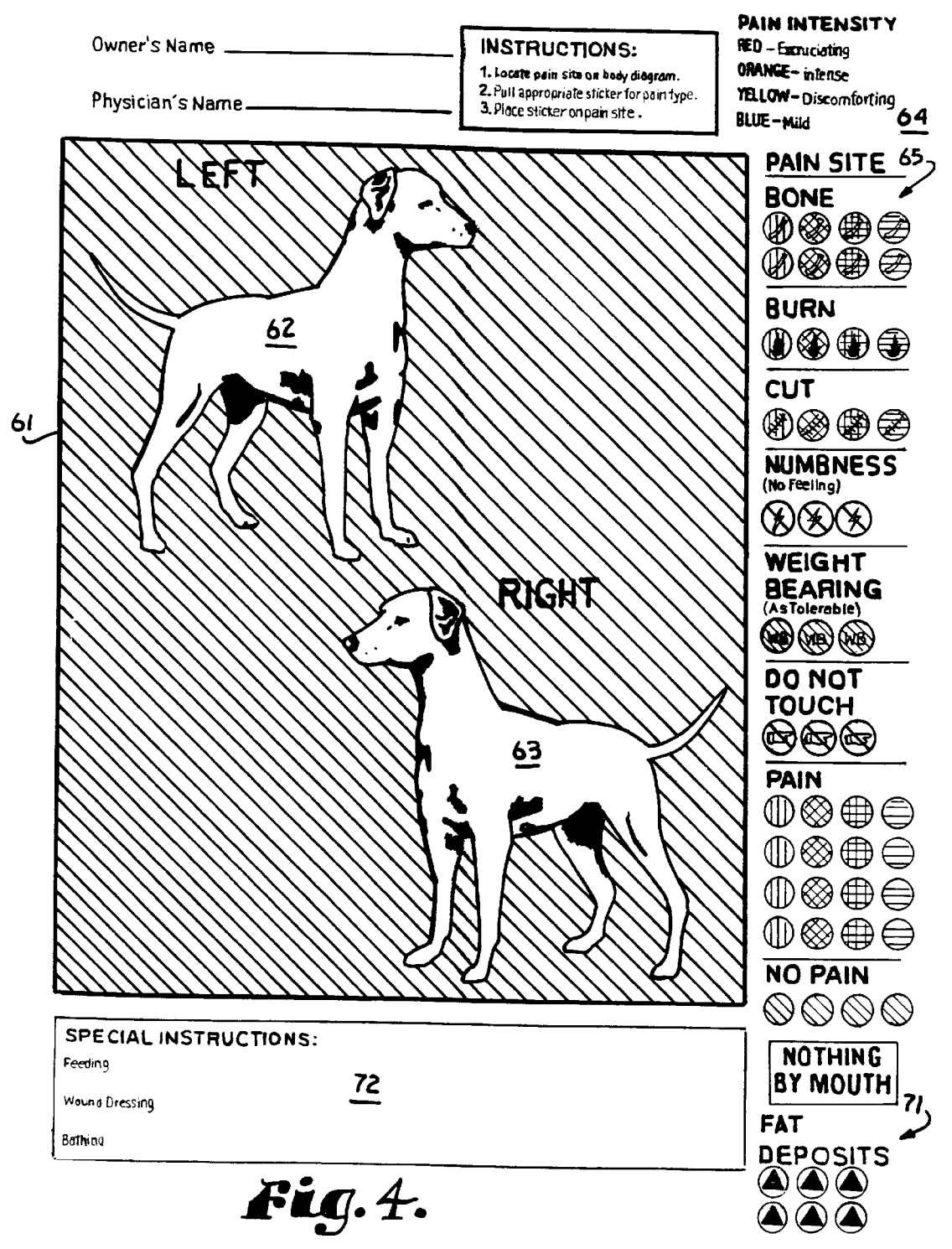

Referring to FIG. 4, a veterinary version of the invention is illustrated. The veterinary version, which can also be implemented as hard copy charts or computerized graphical screen displays, includes a first display area 61 with left and right animal silhouettes 62 and 63, respectively. A second display area 64 includes a number of color coded icon groups, generally indicated at 65. The icon groups 65, again, are essentially identical in form and function to those illustrated in FIGS. 1–3, and will not be further described herein. Additional icon groups which are specially tailored to veterinary use, such as "Fat Deposits" icons 71, can be provided as well. Instead of a row and column time overall pain intensity chart, which, of course, would be relatively useless with an animal patient incapable of self evaluation, a special instructions window 72 is provided for specific operations, such as feeding, wound dressing and bathing, etc.

Figure 6:
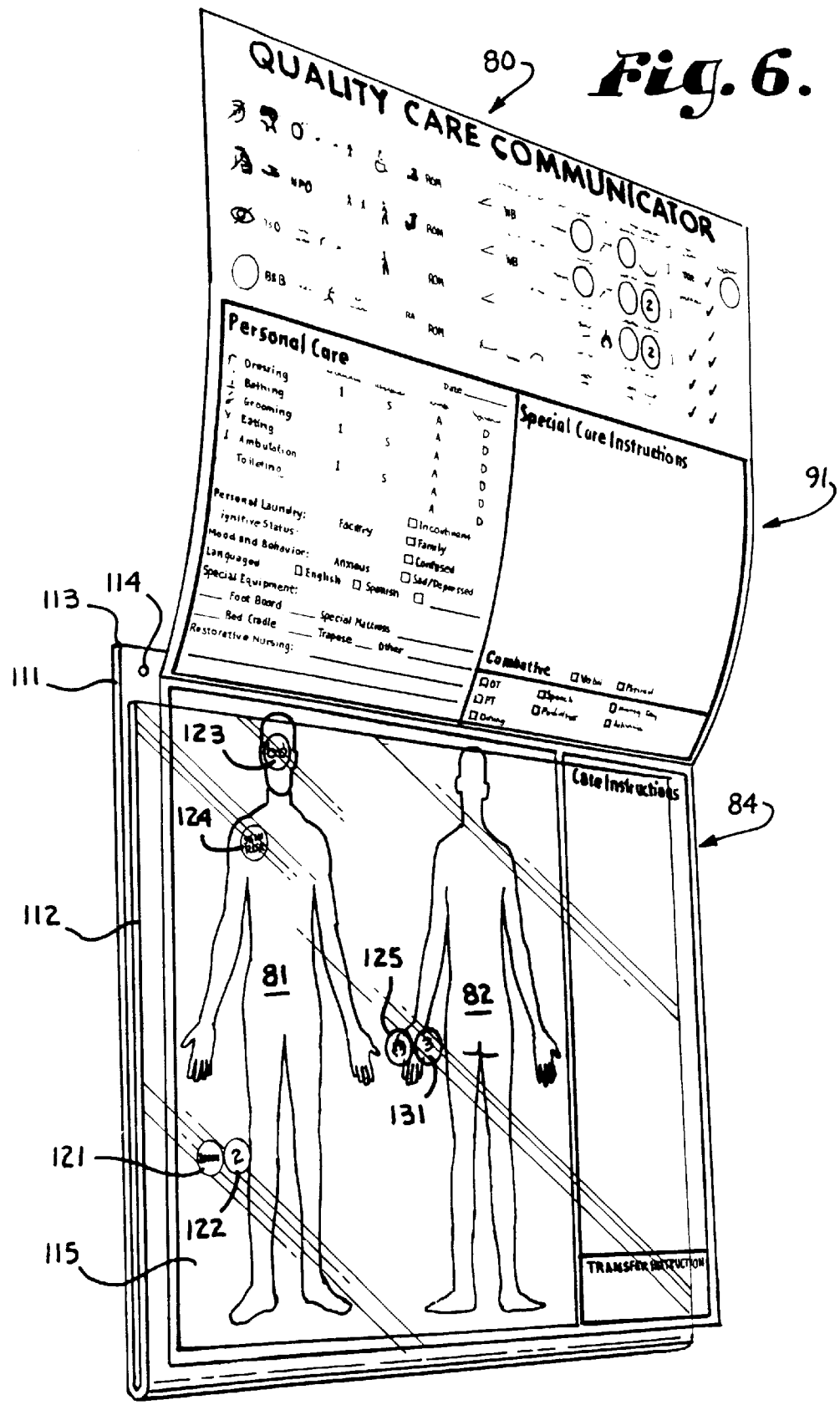
FIG. 6 is a perspective view of a plastic sleeve receiving the folded chart of FIGS. 5a–5c, with icons positioned on the sleeve exterior and the chart.

FIGS. 5a–5c illustrate an alternative hard copy chart, generally indicated at 80. The chart 80 is both a patient pain intensity and location communication apparatus and a comprehensive patient condition indicator. The chart 80, like the chart 1, includes front and back patient silhouettes 81 and 82, respectively, displayed on a colored background 83 in a bottom display area 84 (FIG. 5b). A first group of icons 85 are color coded from yellow to orange to red, and numbered to indicate varying degrees of pain intensity. This first icon group 85 is positioned near the top of the chart 81 in a top display area 91 (FIG. 5a). The top display area 91 is designed to fold over the bottom display area 84 to provide confidentiality, particularly when used with a clear plastic sleeve 92, as shown in FIG. 6.

Also positioned in the top display portion 91 are a second group of icons 93 arrayed along the left side of the top display area 91, which second icon group 93 is indicative of various patient impairments, such as diabetic, dentures, requiring oxygen, etc. A third group of icons 94 is indicative of restorative measures required for this particular patient, such as belt restraint, cane, wheelchair, elbow protector, etc. A fourth group of icons 95 is indicative of various physical conditions of a particular patient, such as broken bones, skin tears, loss of feeling, etc. A fifth icon group 101 includes miscellaneous icons such as check marks and change of condition flags for use in a Personal Care block 102.

The Personal Care block 102 has directions indicating the degree of care required for a particular patient for Dressing, Bathing, Grooming, Eating, Toileting, cognitive status, native language, etc. In addition, a Special Care Instructions block 103 is provided for written special instructions, typically instructions that are subject to frequent change.

A Care Instructions block 104 (FIG. 5*b*) is provided for written instructions for long standing or chronic conditions since the Care Instructions block 104 is positioned within the plastic sleeve 92 while the Special Care Instructions block 103 is placed outside the plastic sleeve 92. A Transfer Instructions block 105 is positioned immediately below the Care Instructions block 104.

FIG. 5*c* illustrates an opposite side of the top display area 91 with an area 105 for personalizing the chart 80 with a particular patient's name and an instruction area 106 indicating the confidentiality of the chart 80 and the circulation restrictions.

FIG. 6 illustrates the use of the transparent plastic sleeve 92 with the folding chart 80. The sleeve 92 includes a back panel 111. A front panel 112 is shorter than the back panel 111, leaving an exposed top portion 113 of the back panel 111 with apertures 114 to enable attachment of the sleeve 92 to a vertical surface (not shown). The bottom display area 84 of the chart 80 is approximately the same dimension as the sleeve front panel 112. The top display area 91 is designed to fold over the sleeve front panel 112 such that it covers the bottom display area 84 to maintain the patient information confidential. Since the sleeve 92 is transparent, the silhouettes 81 and 82 show through the sleeve front panel 112. A front surface 115 of the sleeve front panel 112 thus serves as a temporary location for any of the icons in the chart upper display area 91. For example, a bruise icon 121 with an orange pain intensity icon 122 is shown attached to the front surface 115 for a mild and temporary knee bruise which causes moderate pain. Since these icons 121 and 122 are placed on the outside of the sleeve front panel 112, they can also be sensed tactically by attending nurses or other personnel during low light conditions to determine the existence of any recent temporary changes in patient condition. For example, a night nurse making her first rounds can run her fingers over the sleeve front panel 112 and feel the icons 121 and 122 which will give her an immediate warning a new condition exists of which she should be aware. Conversely, if she feels no icons on the sleeve front panel 112, then she can be assured that only long term patient conditions are relevant.

By contrast, icons representing more permanent conditions, such as a glasses icon 123, a skin risk icon 124 and a serious burn icon 125 causing severe pain represented by a red pain intensity icon 131 are all placed directly on the chart bottom display area 84, which is positioned beneath the sleeve front panel 112. Typically these icons representing more permanent conditions are left in place until the chart 80 is replaced—normally a 90 day cycle.

Figure 7:
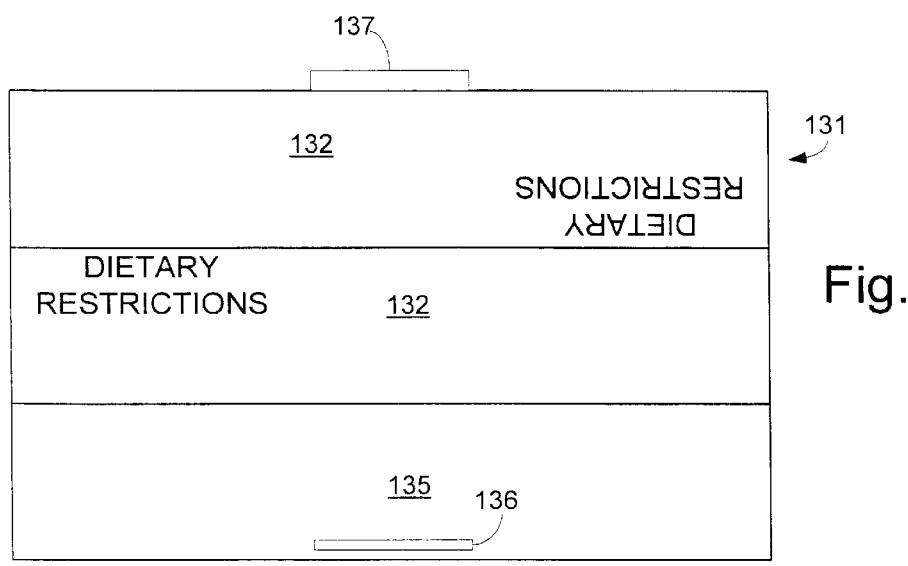
FIG. 7 is a top plan view of a second alternative, folding patient communicator in which a small portable "tent" chart is provided with movable dietary guideline icons.
Figure 8:
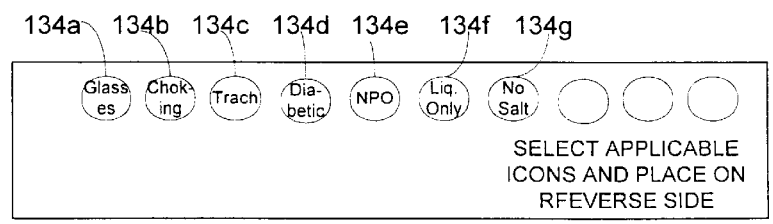
FIG. 8 is a bottom plan view of the second alternative, folding patient communicator in which a small portable "tent" chart is provided with movable dietary guideline icons.

Referring to FIGS. 7 and 8, a second alternative hard copy chart is 131 illustrated. The chart 131 is a dietary supplement chart which is intended as a supplemental to the chart 80 described above. The chart 131 is a small, portable "tent" chart with matching outer surfaces 132 and matching inner surfaces 133. Arrayed on the inner surfaces 133 (only one of which is illustrated in FIG. 8) are a plurality of icon stickers 134, all of which relate to dietary conditions or restrictions. For example, a "choking" icon 134*a*; a "denture" icon 134*b*; a "tracheotomy" icon 134*c*; a "diabetic" icon 134*d*; a "nothing by mouth" icon 134*e*; a "liquids only" icon 134*f*; and a "no sodium" icon 134*g* are pictured. Other icons relating to dietary restrictions will occur to those of ordinary skill in the art. The chart 131 is designed to be a small, e.g. 3" by 2", portable tent when folded in half. Certain pertinent ones of the icons 134*a*–134*g* are removed from the inner surfaces 133 and placed on the outer surfaces 132 by a patient, family member or attendant. The chart 131 is then carried by the patient or attendant to and from meals and placed in front of the patient's chair on the table as a convenient and obvious warning of dietary restrictions and conditions. When not in use, the chart 131 can be conveniently stored by slipping it into the transparent sleeve 92 behind the chart 80. The chart 131 also includes a third panel 135 with a slot 136 which is sized to accommodate a tab 137 to form a "tent" which conveniently sets on a table with both outer surfaces 132 being readily visible to attending personnel.

Figure 9:
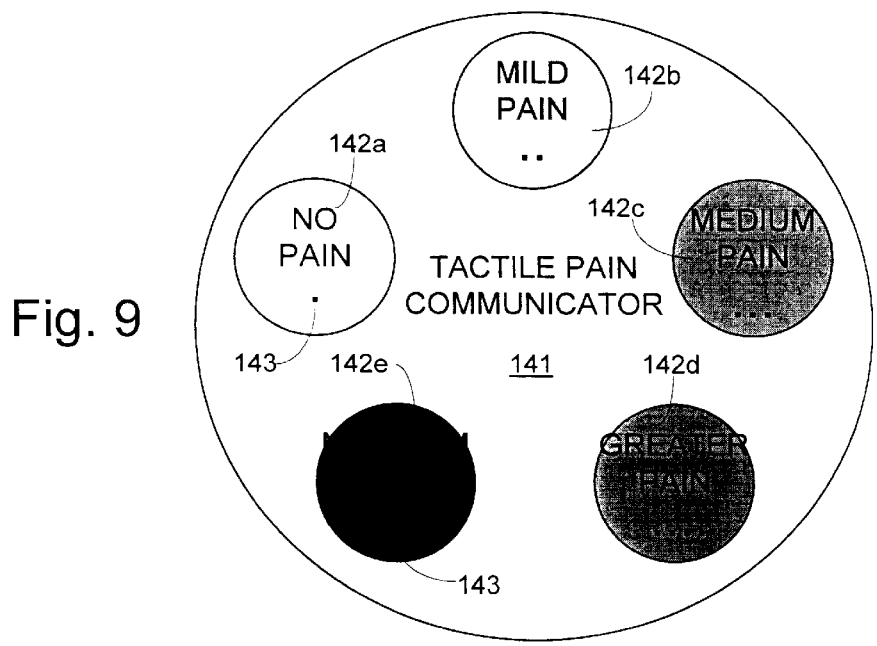
FIG. 9 is a perspective view of a third alternative patient communicator in which a number of touch coded areas are provided, each of which represents a different pain intensity level such that a patient can tactually indicate a pain intensity level.

Referring to FIG. 9, a third alternative embodiment of a hard copy chart is illustrated and generally indicated at 141. The chart 141 is a "tactile pain communicator" for use by patients who, for any reason, are unable to communicate orally with a physician, dentist or other health care provider. The chart 141 includes a number of different tactile pain level indicating areas, here shown as five in number and labeled 142*a*–142*e*. The tactile pain level indicating areas 142*a*–142*e* have printed indicia and are also color coded from blue to red as indications of the pain intensity which they represent. Finally, each tactile pain level indicating area includes a number of raised dots 143 numbering from a single dot 143 in area 142*a* indicating no pain to 5 dots 143 in area 142*e* indicating maximum pain. The chart 141 is useful in a variety of environments, including, without limit, a dentist's office or an oral surgeon's office, and as a pain level communication tool for speech impaired persons. The chart 141 can be small and capable of being held in a patient's hand, for example, 3" in diameter. Alternatively, the chart 141 can be provided as a permanent adjunct to a dental chair, for example placed atop a chair arm or on a frame immediately in line with the patient's vision. When provided as a permanent feature of a dental chair or the like, the indicating areas 142*a*–142*e* can also function as electrical switches which turn on lighted indicators positioned beneath each tactile area.

Figure 10:
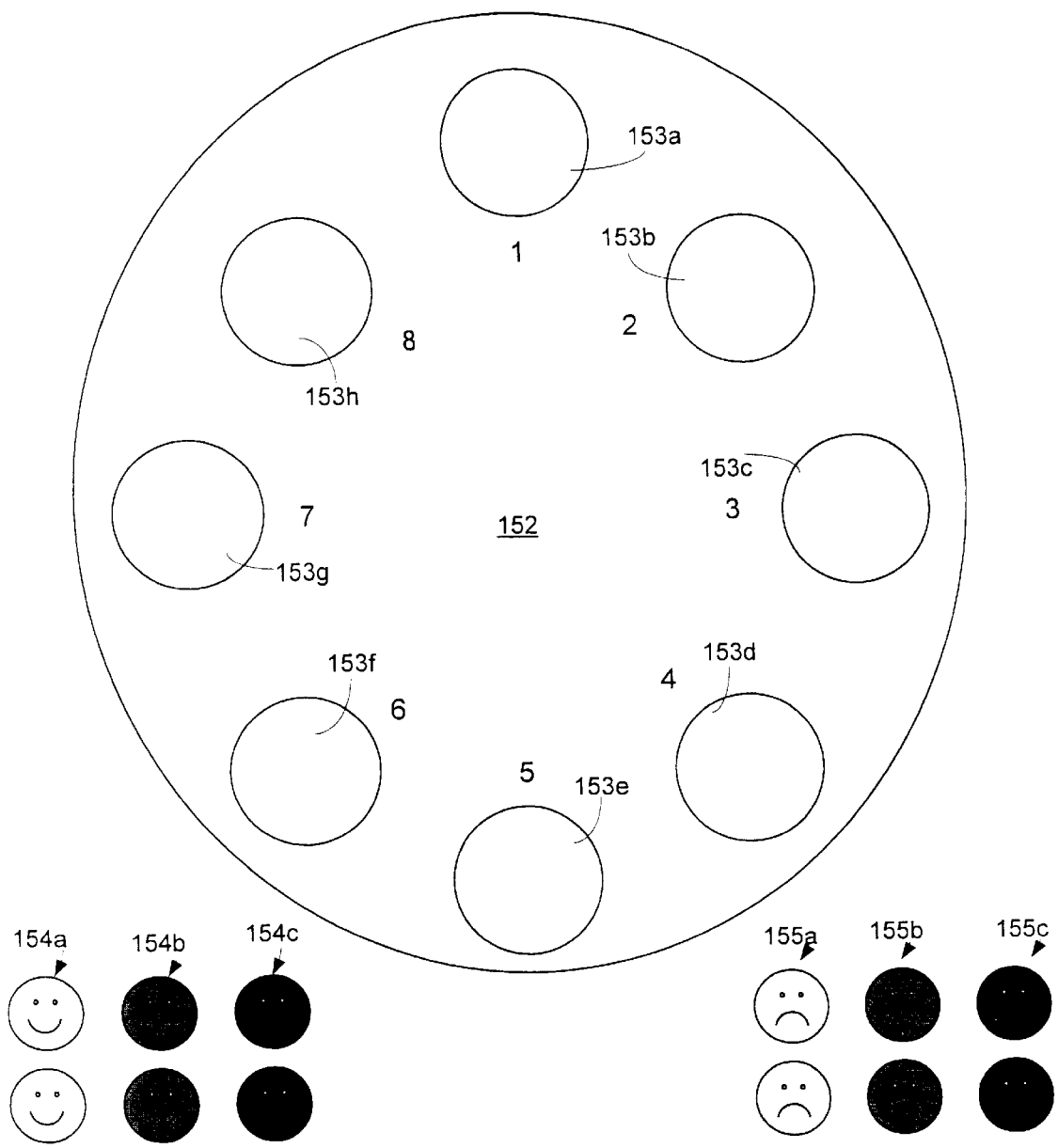
FIG. 10 is a top plan view of a fourth alternative group emotional patient communicator in which a number of transparent areas are provided, one for each person in a group therapy session, with color coded icons movable to the transparent areas to indicate emotional pain and intensity.

Referring to FIG. 10, a fourth alternative hard copy chart, indicated generally at 151, is provided for use in emotional or psychological group or family therapy. The chart 151 includes a larger, opaque circle 152 with a plurality of smaller, transparent windows 153*a*–153*h*, each of which is numbered with a respective number from 1 to 8. A plurality of color coded positive emotional indicating icon stickers 154*a*–154*c* are provided beneath the larger circle 152 on the left side of the chart 151. A plurality of negative emotional pain indicating icon stickers 155*a*–155*c* are positioned on the right side of the chart 151 below the larger circle 152. The icon stickers 154*a*–154*c* and 155*a*–155*c*, although color coded, are preferably transparent or semi-transparent.

The chart 151 is designed to give a therapist or group leader confidential information for use in identifying causes of emotional pain during group or family therapy. During such sessions, each participating member of the group or family is given a number which corresponds to a respective one of the numbers 1 to 8 on the chart 151. Of course, instead of numbers, actual names can be used or family positional names such as Mom, Dad, Sister, Brother, etc. Each participant in the therapy session is given one of the charts 151 and asked, during the sessions, to place pertinent emotional icon stickers 154a–154 and/or 155a–155c from the bottom of their chart 151 onto the applicable transparent window 153a–153h. For example, participants might be asked to select the one person in the group who most makes them feel intimidated, angry or happy and to place an appropriate icon sticker on that person's transparent window 153a–153h. For example, for intimidation or anger, one of the negative icon stickers 155a–155c will be selected according to the intensity of the negative emotion, i.e. yellow stickers 155a represent relatively mild emotions, orange stickers 155b represent stronger feelings and red stickers 155c represent particularly intense feelings. Similarly for positive emotions, white stickers 154a represent somewhat positive feelings, green stickers 154b represent stronger positive feelings and blue stickers 154c represent intensely happy or positive emotions. Once the therapy sessions is over, the therapist collects all of the charts 151 from each participant in confidentiality and overlays them on top of each other. Since the windows 153a–153h are transparent and the icon stickers 154a–154c and 155a–155c are semi-transparent, the therapist can quickly discern the person or persons who are the primary source of the negative and/or positive emotional feelings for the participants. Therapy for the group and for individuals in the group can then be devised accordingly.

Any of the charts 80, 131, 141 or 151 can also be implemented as screen displays in a computer program and the claims are intended to cover such an embodiment.

It should be noted that the charts and screen displays illustrated in FIGS. 1–10 and described herein are exemplary only and that many other variations can be devised. For example, the illustrated silhouettes 2 and 3 represent an adult male, but it is contemplated that other charts with representations of an adult female or male or female children can be used. The icon groupings are also not limited to those shown, but can include other symbols, either of conventional or custom design. In the veterinary version, a silhouette of a dog is illustrated as representative, but other versions including cats, horses and other domestic animals and pets are contemplated. The colors used in the pain intensity, emotional pain intensity icons and other color coding are also representative only, since many other color schemes can be used, although the gradations from blue to red are somewhat accepted in the field. The numbers of degrees of pain represented on the charts 1, 42, 80, 141 and 151, either physical or emotional is also representative only, and can be expanded or lessened as well.

It is thus to be understood that while certain forms of the present invention have been illustrated and described herein, it is not to be limited to the specific forms or arrangement of parts described and shown.

What is claimed and desired to be secured by Letters Patent is as follows:

1. A patient condition communication apparatus comprising:
   a) a graphic display medium including:
      i) a first display area on a bottom portion of said display medium including at least one graphic image representing at least a portion of a human body;
      ii) a second display area on a top portion of said display medium including a plurality of icons representing particular patient conditions, said icons being movable from said second display area to said first display area such that they can be positioned on said body graphic image to indicate patient conditions, said second display area being foldable over said first display area to thereby provide confidentiality for said patient condition communication apparatus.

2. A patient condition communication apparatus as in claim 1, wherein at least some of said icons are color coded with different colors representing different pain intensities.

3. A patient condition communication apparatus as in claim 1, and further comprising:
   a) a sleeve with a back panel and a transparent front panel;
   b) a space between said sleeve back panel and front panel sized to receive said bottom display portion of said graphic display medium wherein said bottom display portion of said graphic display medium is covered by said front display panel and said top display portion of said graphic display medium can be folded over to conceal said transparent front panel and said bottom portion of said graphic display medium.

4. A patient condition communication apparatus as in claim 3, wherein:
   a) said sleeve front panel has an outer surface;
   b) said icons are movable to said sleeve front panel outer surface in a position overlying said body portion graphic image of said graphic display medium inserted into said sleeve to indicate a temporary patient condition; and
   c) said icons are movable directly to said body portion graphic image of said graphic display medium inserted into said sleeve to indicate a more permanent patient condition.

5. A patient condition communication apparatus as in claim 4, wherein icons placed on said sleeve front panel outer surface can be tactually sensed to give an immediate indication of any temporary patient conditions in low light conditions.

6. A patient condition communication apparatus as in claim 1, wherein said plurality of icons representing particular patient conditions includes a group of icons which are coded to indicate varying degrees of pain intensity.

7. A patient condition communication apparatus as in claim 1, wherein said plurality of icons representing particular patient conditions includes a plurality of groups of icons including one or more of the following:
   a) various patient impairments, such as diabetic, dentures, requiring oxygen;
   b) restorative measures required for this particular patient, such as belt restraint, cane, wheelchair, elbow protector; and
   c) various physical conditions of a particular patient, such as broken bones, skin tears, loss of feeling.

8. A patient condition communication apparatus as in claim 1, wherein said graphic display medium includes, on said top portion thereof, a Personal Care block with preprinted selectable instructions indicating the degree of care required for a particular patient for Dressing, Bathing, Grooming, Eating, Toileting, cognitive status, native language, etc.

9. A patient condition communication apparatus as in claim 1, wherein said graphic display medium includes, on said top portion thereof, a Special Care Instructions block provided for written special instructions which are subject to change.

10. A patient condition communication apparatus as in claim 1, wherein said graphic display medium includes, on said bottom portion thereof, a Care Instructions block provided for written special instructions which are longstanding.

11. A patient condition communication apparatus as in claim 1, wherein said graphic display medium includes, on said bottom portion thereof, a Transfer Instructions block.

12. A patient condition communication apparatus comprising:
   a) a graphic display medium including:
      i) a first display area on a bottom portion of said display medium including at least one graphic image representing at least a portion of a human body;
      ii) a second display area on a top portion of said display medium including a plurality of icons representing particular patient conditions, said icons being movable from said second display area to said first display area such that they can be positioned on said body graphic image to indicate patient conditions, said second display area being foldable over said first display area to thereby provide confidentiality for said patient condition communication apparatus;
   b) a sleeve with a back panel and a transparent front panel;
   c) a space between said sleeve back panel and front panel sized to receive said bottom display portion of said graphic display medium wherein said bottom display portion of said graphic display medium is covered by said front display panel and said top display portion of said graphic display medium can be folded over to conceal said transparent front panel and said bottom portion of said graphic display medium.

13. A patient condition communication apparatus as in claim 12, wherein:
   a) said sleeve front panel has an outer surface;
   b) said icons are movable to said front panel outer surface in a position overlying said body portion graphic image of said graphic display medium inserted into said sleeve to indicate a temporary patient condition; and
   c) said icons are movable directly to said body portion graphic image of said graphic display medium inserted into said sleeve to indicate a more permanent patient condition.

14. A patient condition communication apparatus as in claim 13, wherein icons placed on said sleeve front panel outer surface can be tactually sensed to give an immediate indication of any temporary patient conditions in low light conditions.

15. A patient condition communication apparatus as in claim 12, wherein at least some of said icons are color coded with different colors representing different pain intensities.

16. A patient condition communication apparatus as in claim 12, wherein said plurality of icons representing particular patient conditions includes a plurality of groups of icons including one or more of the following:
   a) various patient impairments, such as diabetic, dentures, requiring oxygen;
   b) restorative measures required for this particular patient, such as belt restraint, cane, wheelchair, elbow protector; and
   c) various physical conditions of a particular patient, such as broken bones, skin tears, loss of feeling.

17. A patient condition communication apparatus as in claim 12, wherein said graphic display medium includes, on said top portion thereof, a Personal Care block with preprinted selectable instructions indicating the degree of care required for a particular patient for Dressing, Bathing, Grooming, Eating, Toileting, cognitive status, native language, etc.

18. A patient condition communication apparatus as in claim 12, wherein said graphic display medium includes, on said top portion thereof, a Special Care Instructions block provided for written special instructions which are subject to change.

19. A patient condition communication apparatus as in claim 11, wherein said graphic display medium includes, on said bottom portion thereof, a Care Instructions block provided for written special instructions which are longstanding.

20. A patient condition communication apparatus comprising a folding portable chart with first and second legs, each having an outer surface and an inner surface and including:
   a) a first display area on at least one of said outer surfaces with an area sized to accommodate a plurality of icons indicating dietary conditions and/or restrictions for a particular patient; and
   b) a second display area on at least one of said inner surfaces including a plurality of icons representing patient dietary conditions and restrictions, said icons being selectively movable from said second display area to said first display area such that the apparatus can be customized for a particular patient and placed on an eating surface near the patient.

21. A patient condition communication apparatus as in claim 20, said portable chart further comprising a third leg attached to one of said first or second legs and removably attachable to the other of said first and second legs, said first, second and third legs forming a self supporting tent with said outer surfaces being readily visible.

22. A patient condition communication apparatus as in claim 20, wherein said icons include one or more of the following:
   a) a "choking" icon;
   b) a "denture" icon;
   c) a "tracheotomy" icon;
   d) a "diabetic" icon;
   e) a "nothing by mouth" icon;
   f) a "liquids only" icon; and
   g) a "no sodium" icon.

23. A tactile patient condition communication apparatus comprising a chart with a plurality of pain intensity indicating areas, each of said areas being coded to indicate a different respective pain intensity condition, all of said indicating areas being included in an area small enough such that a patient can select any one of the areas by pointing to it with a finger to indicate their particular pain condition to an observer.

24. A tactile patient condition communication apparatus as in claim 23, wherein said areas are pain intensity coded by color.

25. A tactile patient condition communication apparatus as in claim 23, wherein said areas are pain intensity coded by different respective raised patterns.

26. A group therapy communication apparatus comprising a portable chart including:
   a) a first display area with a plurality of removable icons indicating different respective emotions and/or emotional intensity levels; and b) a second display area with a plurality of transparent windows, each of which can be designated to represent a different participant in a group therapy session, wherein c) participants in the group therapy session can selectively remove icons from said first area and affix them to selected window(s) on said second display area to indicate emotional response levels associated with that participant.

27. A group therapy communication apparatus as in claim 26, wherein said icons are at least semi-transparent such that multiple stacked icons can be seen when several charts are overlaid on top of each other.

28. A group therapy communication apparatus as in claim 26, wherein said icons are coded by color to indicate different respective emotional and/or emotional intensity levels.

* * * * *